United States Patent

Tsujihara et al.

[11] Patent Number: 5,565,569
[45] Date of Patent: Oct. 15, 1996

[54] ELLIPTICINE DERIVATIVE AND PROCESS FOR PREPARING THE SAME

[75] Inventors: Kenji Tsujihara; Naoyuki Harada, both of Urawa; Kunihiko Ozaki, Higashimurayama; Motoaki Ohashi, Kawaguchi; Koji Oda, Urawa, all of Japan

[73] Assignee: Tanabe Seiyaku Co., Ltd., Osaka, Japan

[21] Appl. No.: 186,016

[22] Filed: Jan. 25, 1994

[30] Foreign Application Priority Data

Jan. 25, 1993 [JP] Japan .................................. 5-013441

[51] Int. Cl.⁶ .................................................. A61K 31/475
[52] U.S. Cl. ........................................................... 546/70
[58] Field of Search ............................. 514/285; 546/70

[56] References Cited

U.S. PATENT DOCUMENTS

| | | | |
|---|---|---|---|
| 3,933,827 | 1/1976 | Brossi et al. | 546/70 |
| 4,310,667 | 1/1982 | LePeco et al. | 546/70 |
| 4,698,423 | 10/1987 | Honda et al. | 546/70 |
| 5,272,146 | 12/1993 | Haugwitz | 546/70 |
| 5,407,940 | 4/1995 | Bisagni | 514/285 |
| 5,441,941 | 8/1995 | Haugwitz | 514/285 |

FOREIGN PATENT DOCUMENTS

| | | | |
|---|---|---|---|
| 365176 | 4/1990 | European Pat. Off. | 546/70 |
| 5-310736 | 11/1993 | Japan | 546/70 |
| 1508388 | 4/1976 | United Kingdom . | |

OTHER PUBLICATIONS

The Merck Index, An Encyclopedia of Chemicals, Drugs, and Biologicals, Tenth Edition, p. 3511, (1983).

The Alkaloids Chemistry and Pharmacology, vol. XXV, p. 141, (1985).

Ratcliffe et al. Jour. Chem Soc Perkins I, (1988) pp. 2933–2943.

*Primary Examiner*—Donald G. Daus
*Attorney, Agent, or Firm*—Finnegan, Henderson, Farabow, Garrett & Dunner, L.L.P.

[57] ABSTRACT

An ellipticine derivative of the formula [I]:

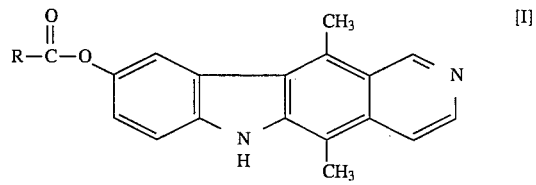

wherein R is a substituted lower alkyl group, a substituted or unsubstituted lower alkoxy group or a heteromonocyclic group, or a pharmaceutically acceptable salt thereof, which show excellent antitumor activity, less side effects, less toxicity and/or high solubility in water and are useful as antitumor agent, and a process for preparing the same.

3 Claims, No Drawings

ELLIPTICINE DERIVATIVE AND PROCESS FOR PREPARING THE SAME

The present invention relates to a novel ellipticine derivative which is useful as an antitumor agent, and a process for preparing the same.

PRIOR ART

It has been known that 2-methyl-9-hydroxyellipticinium acetate can be used as an antitumor agent, for example, in the treatment of breast cancers (cf. The Merck Index, Tenth edition, p. 512). However, this compound has various problems. For example, the pharmacological activity thereof is insufficient, i.e. it does not show enough macrobiotic activity on mice with Lewis lung carcinoma, and this compound has significant side effects such as pulsus frequens, and strong toxicity. Besides, although 9-hydroxyellipticine hydrochloride shows more excellent antitumor activity than ellipticine, the solubility in water thereof is low, and hence, it cannot be useful in clinical use [*The Alkaloids Chemistry and Pharmacology*; Edited by Arnold Brossi; Academic Press Inc. (London) Ltd.; Volume XXV, p 141 (1985)].

On the other hand, there have been known 9-hydroxyellipticine derivatives having a substituent such as acetyl group or propanoyl group on 9-hydroxy group (cf. U.S. Pat. No. 3,933,827).

BRIEF DESCRIPTION OF THE INVENTION

An object of the present invention is to provide a novel ellipticine derivative having excellent antitumor activity, less side effects, less toxicity, and/or the high solubility in water. Another object of the present invention is to provide a process for preparing thereof.

DETAILED DESCRIPTION OF THE INVENTION

The present invention relates to an ellipticine derivative of the formula [I]:

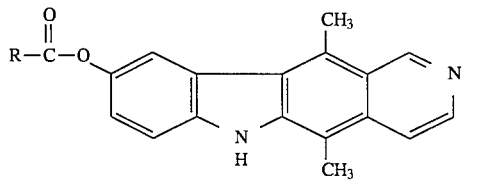

wherein R is a substituted lower alkyl group, a substituted or unsubstituted lower alkoxy group or a heteromonocyclic group, or a pharmaceutically acceptable salt thereof.

The ellipticine derivatives of the present invention and a pharmaceutically acceptable salt thereof have excellent antitumor activity and are useful as an antitumor agent.

The "substituted lower alkyl group" for R includes, for example, a lower alkyl group substituted by 1 to 3 groups selected from a substituted or unsubstituted lower alkoxy group, a protected or unprotected carboxyl group, a substituted or unsubstituted lower alkoxycarbonyl group, a substituted or unsubstituted phenyl group, a protected or unprotected aminocarbonyl group, a protected or unprotected amino group, a protected or unprotected amino-substituted lower alkanoylamino group and a protected or unprotected hydroxy group, more particularly, a lower alkyl group substituted by 1 to 3 groups selected from a lower alkoxy group, a lower alkoxy-substituted lower alkoxy group, a protected or unprotected carboxyl-substituted lower alkoxy group, a protected or unprotected carboxyl group, a lower alkoxycarbonyl group, a lower alkoxy-substituted lower alkoxycarbonyl group, a protected or unprotected carboxyl-substituted lower alkoxycarbonyl group, a protected or unprotected aminocarbonyl group, a protected or unprotected amino group, a protected or unprotected amino-substituted lower alkanoylamino group and a protected or unprotected hydroxy group. Among them, lower alkyl groups substituted by 1 to 3 groups selected from a lower alkoxy group, a lower alkoxy-substituted lower alkoxy group, a carboxyl-substituted lower alkoxy group, carboxyl group, a lower alkoxycarbonyl group, a lower alkoxy-substituted lower alkoxycarbonyl group, a carboxy-substituted lower alkoxycarbonyl group, aminocarbonyl group, a lower alkylaminocarbonyl group, amino group, a lower alkylamino group, formylamino group, an amino-substituted lower alkanoylamino group and hydroxy group are more preferable.

The "a substituted or unsubstituted lower alkoxy group" for R is, for example, a lower alkoxy group which may optionally be substituted by 1 to 3 groups selected from a substituted or unsubstituted lower alkoxy group, a protected or unprotected carboxyl group, a substituted or unsubstituted lower alkoxycarbonyl group, a protected or unprotected aminocarbonyl group, a protected or unprotected amino group, a protected or unprotected amino-substituted lower alkanoylamino group and a protected or unprotected hydroxy group, and among them, a lower alkoxy group and a lower alkoxy-substituted lower alkoxy group are more preferable.

The "heteromonocyclic group" for R is a heteromonocyclic group having 1 to 3 heteroatoms selected from nitrogen atom and sulfur atom, for example, thiazolyl group, isothiazolyl group, or thiazolidinyl group. Among them, thiazolidinyl group is more preferable.

Among the compounds [I] of the present invention, the pharmacologically preferable compounds are compounds of the formula [I] wherein R is a lower alkyl group which is substituted by a protected or unprotected carboxyl group or the group of the formula [II]:

which R is the same as defined above) is an amino acid residue. The amino acid residue includes a group which is obtained by removing hydroxy group from the carboxyl group of a corresponding amino acid such as glycine, alanine, serine, phenylalanine, valine, lysine, isoleucine, aspartic acid, glutamic acid, asparagine, glutamine, or the like, and the amino acid residues of aspartic acid, glutamic acid, asparagine and glutamine are more preferable. Besides, the functional groups in these amino acid residues, e.g. amino group, carboxyl group, hydroxy group, may optionally be protected by a conventional protecting group which is used in this field.

More preferable compounds are those of the formula [I] wherein R is a lower alkyl group which is substituted by a protected or unprotected carboxyl group. Further preferable compounds are those of the formula [I] wherein R is an alkyl group substituted by carboxyl group, and those wherein R is a propyl group substituted by carboxyl group are most preferable.

When the group of R has an asymmetric carbon atom, the present compound [I] may exist in the form of optical isomers. The present invention includes within its scope either one of these optical isomers and a mixture thereof.

The "protected carboxyl group" includes esterified carboxyl groups. The ester residue thereof includes, for example, a lower alkyl group, a halogen-substituted lower alkyl group, a phenyl-lower alkyl group, phenacyl group, and the like.

The "protected amino group" includes amino groups protected by a conventional protecting group for amino group, for example, ones protected by formyl group, a lower alkanoyl group, a lower alkyl group, a lower alkoxycarbonyl group, or a phenyl-lower alkoxycarbonyl group. Among them, amino groups protected by formyl group, a lower alkanoyl group or a lower alkyl group are more preferable.

The "protected hydroxy group" includes ones protected by a conventional protecting group, for example, hydroxy group protected by a lower alkoxycarbonyl group, a halogeno-lower alkoxycarbonyl group, a phenyl-lower alkyl group, a tri-lower alkylsilyl group, or a phenyl-lower alkoxycarbonyl group.

The compounds [I] of the present invention may be used as a medicine either in the free form or in the form of a pharmaceutically acceptable salt thereof. The pharmaceutically acceptable salt is, for example, salts with an inorganic acid (e.g. hydrochloride, sulfate, etc.), salts with an organic acid (e.g. a lower alkylsulfonate, acetate, etc.), alkali metal salts (e.g. sodium salt, potassium salt, etc.), alkaline earth metal salts (e.g. calcium salt, etc.), and the like.

The compounds [I] and a pharmaceutically acceptable salt thereof may be administered either by oral route or parenteral route, and may be used in the form of a conventional pharmaceutical preparation, for example, tablets, granules, capsules, powders, injections, and the like, if necessary, in admixture with pharmaceutically acceptable carrier, diluent or disintegrant.

The dosage of the compound [I] of the present invention varies according to administration routes and ages, weights and conditions of the patients, but it is usually in the range of about 0.1 to 50 mg/kg/day, preferably in the range of about 1 to 10 mg/kg/day.

The compound [I] of the present invention may be prepared by reacting 9-hydroxyellipticine or a salt thereof with a carboxylic acid compound of the formula [IV]:

$$R^1COOH \qquad [IV]$$

wherein $R^1$ is a substituted lower alkyl group, a substituted or unsubstituted lower alkoxy group or a heteromonocyclic group and when said substituents for these groups have an amino group, carboxyl group or hydroxy group, these substituents may optionally be protected, or a salt thereof, or a reactive derivative thereof, to give an ellipticine derivative of the formula [III]:

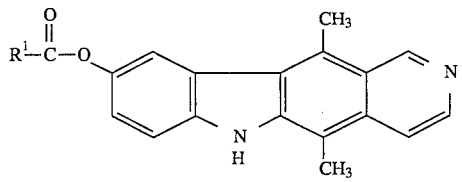

wherein $R^1$ is the same as defined above, and when $R^1$ has a protected amino group, a protected carboxyl group or a protected hydroxy group, followed by subjecting the compound [III] to de-protecting reaction to remove these protecting groups, if necessary.

The reaction of 9-hydroxyellipticine or a salt thereof with the free compound [IV] or a salt thereof may be carried out in the presence or absence of a condensing agent in a suitable solvent. The solvent includes any one which does not affect the reaction, for example, acetone, dimethylformamide, and the like. The condensing agent includes, for example, dicyclohexylcarbodiimide, 1-ethyl-3-(3-dimethylaminopropyl)carbodiimide, 1,1'-carbonyldiimidazole, and the like. On the other hand, the reaction of 9-hydroxyellipticine or a salt thereof with a reactive derivative of the compound [IV] may be carried out in the presence or absence of an acid-acceptor in a suitable solvent. The acid-acceptor includes inorganic or organic basic compounds, for example, an alkali metal hydroxide, an alkali metal carbonate, pyridine, a tri-lower alkylamine, etc. The reactive derivative of the carboxylic acid compound [IV] is, for example, an acid halide (e.g. acid chloride, etc.), an acid anhydride, an active ester, and the like. The solvent may be any one which does not affect the reaction. The above reactions may preferably be carried out at a temperature from under cooling to with warming (e.g. 20° to 50° C.).

When the carboxylic acid compound [IV] or a reactive derivative thereof has a protected amino group, a protected carboxyl group or a protected hydroxy group, the protecting groups may be any conventional ones for amino group, carboxyl group or hydroxy group, respectively. The protecting group for amino group is, for example, formyl group, a lower alkanoyl group, a lower alkyl group, a lower alkoxycarbonyl group and a phenyl-lower alkoxycarbonyl group. The protecting group for carboxyl group is an ester residue such as a lower alkyl group, a halogeno-lower alkyl group, a phenyl-lower alkyl group, phenacyl group, and the like. The protecting group for hydroxy group is, for example, a lower alkoxycarbonyl group, a halogeno-lower alkoxycarbonyl group, a phenyl-lower alkyl group, a tri-lower alkylsilyl group, a phenyl-lower alkoxycarbonyl group, and the like.

The removal of the protecting groups for amino group, carboxyl group or hydroxy group may be carried out by a conventional method such as reduction, acid-treatment, solvolysis, and the like, and the method for removal of the protecting group may be selected according to the types of the protecting groups.

The above reactions can proceed without racemization, and when an optically active carboxylic acid compound [IV] is used in these reactions, there is obtained optically active compound [I].

The ellipticine derivatives [I] of the present invention and a pharmaceutical acceptable salt thereof show excellent antitumor activity, and are useful for the treatment of various tumors is warm-blooded animals including human beings. For example, the ellipticine derivatives [I] of the present invention and a pharmaceutical acceptable salt thereof show significant antitumor activity and macrobiotic activity on mice inoculated with sarcoma 180 cells, mouse leukemia P 388 cells, mouse colon 26 cells, mouse Lewis lung carcinoma cells and B16 melanoma. Besides, the ellipticine derivatives [I] of the present invention and a pharmaceutical acceptable salt thereof show inhibitory activity against p53 protein-linked kinases; i.e. DNA-activated kinase, casein kinase, cdc2 kinase, thereby causing a specific inhibitor of p53 protein phosphorylation, followed by induction of apoptosis of cancer cells in which mutant p53 is overexpressed [Normal cells in which p53 is little expressed are resistent to the compounds of the present invention].

The ellipticine derivatives [I] of the present invention and a pharmaceutically acceptable salt thereof have high solubility in water. In addition, the ellipticine derivatives [I] of the present invention and a pharmaceutical acceptable salt thereof show less side effects on circulatory system, e.g. pulsus frequens, and low toxicity. For example, when 9-(4-carboxylbutyryloxy)ellipticine hydrochloride was administered intravenously to mice in an amount of 80 mg/kg/day for 7 day, no mouse died for 7 days thereafter.

Throughout the present description and claims, the "lower alkyl group" and the "lower alkoxy group" mean ones having 1 to 6 carbon atoms, more preferably 1 to 4 carbon atoms, respectively. The "lower alkanoyl group" means ones having 2 to 6 carbon atoms, preferably 2 to 4 carbon atoms.

EXAMPLES

The present invention is illustrated in more detail by the following Examples, but should not be construed to be limited thereto.

EXAMPLE 1

(1) To acetone (80 ml) are added 9-hydroxyellipticine (1.31 g) and anhydrous potassium carbonate (6.9 g), and thereto is added dropwise methoxyacetic chloride (815 mg) with stirring. The mixture is reacted at room temperature for 5 hours, and thereto is added dimethylformamide (20 ml). The mixture is stirred, filtered, and the filtrate is concentrated under reduced pressure. The residue is purified by silica gel column chromatography (solvent; chloroform-methanol) to give 9-methoxyacetoxyellipticine (823 mg) as yellow powder.
Yield: 49%

(2) The above product (823 mg) is dissolved in a mixture of chloroform-methanol (1:1) (100 ml), and thereto is added methanesulfonic acid (260 mg). The mixture is stirred for 10 minutes, and evaporated under reduced pressure to remove the solvent. To the residue is added ether, and the precipitated powder is collected by filtration, washed, and dried to give 9-methoxyacetoxyellipticine methanesulfonate (988 mg) as yellow powder.
Yield: 93%
FAB-MS (m/z): 335 (MH$^+$, hereinafter, M means a free base)
NMR (DMSO-$d_6$) δ: 2.40 (3H, s), 2.79 (3H, s), 3.21 (3H, s), 3.48 (3H, s), 4.45 (2H, s), 7.43 (1H, dd, J=2.0, 8.8 Hz), 7.63 (1H, d, J=8.8 Hz), 8.18 (1H, J=2 Hz), 8.39 (2H, m), 9.84 (1H, s), 11.81 (1H, NH), 15.1 (1H, brs)

EXAMPLE 2

(1) To dimethylformamide (60 ml) are added 2-methoxypropionic acid (500 mg), 1-hydroxybenzotriazole (648 mg) and dicyclohexylcarbodiimide (1.19 g), and the mixture is stirred at room temperature for 4 hours. To the mixture are added 9-hydroxyellipticine hydrochloride (1.20 g) and triethylamine (486 mg), and the mixture is stirred at room temperature overnight. To the reaction solution is added ethyl acetate (300 ml), and the mixture is stirred. The insoluble materials are removed by filtration, and the filtrate is washed with 2% aqueous potassium carbonate solution and saturated saline solution, dried, and concentrated under reduced pressure. The residue is purified by silica gel column chromatography (solvent; chloroform-methanol) to give 9-(2-methoxypropionyloxy)ellipticine (960 mg) as yellow powder.
Yield: 69%

(2) The above product (960 mg) and methanesulfonic acid (264 mg) are treated in the same manner as in Example 1-(2) to give 9-(2-methoxypropionyloxy)ellipticine methanesulfonate (1178 mg) as yellow powder.
Yield: 96%
FAB-MS (m/z): 349 (MH$^+$)
NMR (DMSO-$d_6$) δ: 1.56 (3H, d, J=6.8 Hz), 2.39 (3H, s), 2.78 (3H, s), 3.21 (3H, s), 3.48 (3H, s), 4.31 (1H, q, J=6.8 Hz), 7.41 (1H, dd, J=2.2, 8.6 Hz), 7.63 (1H, d, J=8.6 Hz), 8.13 (1H, d, J=2.2 Hz), 8.36 (1H, d, J=7.1 Hz), 8.42 (1J=7.1 Hz), 9.90 (1H, s), 12.11 (1H, NH)

EXAMPLES 3–8

The corresponding starting compounds are treated in the same manner as in Example 1 or 2 to give the compounds as listed in Table 1.

TABLE 1

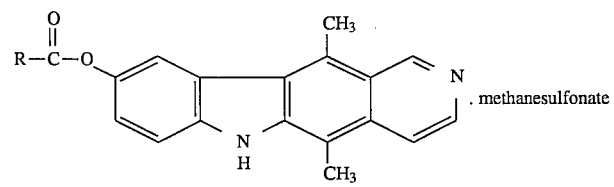

. methanesulfonate

| Ex. No. | RCO— | Physical Properties |
|---|---|---|
| 3 | CH$_3$O—C(CH$_3$)(CH$_3$)—CO— | Yield: 66% (based on 9-hydroxyellipticine)<br>Yellow powder<br>FAB-MS (m/z): 363 (MH$^+$)<br>NMR (DMSO-$d_6$) δ: 1.60 (6H, s), 2.38 (3H,s), 2.81 (3H,s), 3.24 (3H, s), 3.38 (3H, s), 7.40 (1H, dd, J=2.2, 8.7 Hz), 7.64 (1H, d, J =8.7 Hz), 8.12 (1H, d, J=2.2 Hz), 8.39 (1H, d, J=7.1 Hz), 8.43 (1H, d, J=7.1 Hz), 9.93 (1H, s), 12.14 (1H, NH) |
| 4 | CH$_3$OCH$_2$CH$_2$CO— | Yield: 38% (based on 9-hydroxyellipticine)<br>Yellow Powder<br>EI-MS (m/z): 348 (M$^+$)<br>NMR (DMSO-$d_6$) δ: 2.39 (3H, s), 2.78 (3H, s), 2.93 (2H, t, J=6.2 Hz), 3.19 (3H, s), 3.36 (3H, s), 3.76 (2H, t, J=6.2 Hz), 7.36 (1H, dd, J=2.2, 8.7 Hz), 7.62 (1H, d, J=8.7 Hz), 8.09 (1H, d, J=2.2 |

TABLE 1-continued

Structure: R—C(=O)—O— attached to ellipticine core (9-position) with CH₃ groups at 5,11 positions, NH, pyridine N. · methanesulfonate

| Ex. No. | RCO— | Physical Properties |
|---|---|---|
| | | Hz), 8.36 (1H, d, J=6.9 Hz), 8.41 (1H, d, J=6.9 Hz), 9.89 (1H, s), 12.10 (1H, NH) |
| 5 | $CH_3OCH_2CH_2$—$OCH_2CO$— | Yield: 43% (based on 9-hydroxyellipticine)<br>Yellow Powder<br>FAB-MS (m/z): 379 (MH⁺)<br>NMR (DMSO-$d_6$) δ: 2.42 (3H, s), 2.75 (3H, s), 3.17 (3H, s), 3.32 (3H, s), 3.56 (2H, m), 3.78 (2H, m), 4.53 (2H, s), 7.40 (1H, m), 7.60 (1H, d, J=8.3 Hz), 8.14 (1H, d, J=2.0 Hz), 8.36 (2H, m), 9.86 (1H, s), 12.07 (1H, s), 15.0 (1H, brs) |
| 6 | $CH_3OCO$— | Yield: 22% (based on 9-hydroxyellipticine)<br>Yellow Powder<br>FAB-MS (m/z): 321 (MH⁺)<br>NMR (DMSO-$d_6$) δ: 2.34 (3H, s), 2.86 (3H, s), 3.29 (3H, s), 3.90 (3H, s), 7.53 (1H, dd, J=2, 8.8 Hz), 7.68 (1H, d, J=8.8 Hz), 8.33 (1H, d, J=2 Hz), 8.45 (2H, s), 9.98 (1H, s), 12.22 (1H, s), 15.08 (1H, brs) |
| 7 | $CH_3O(CH_2)_2OCO$— | Yield: 18% (based on 9-hydroxyellipticine)<br>Yellow Powder<br>FAB-MS (m/z): 365 (MH⁺)<br>NMR (DMSO-$d_6$) δ: 2.35 (3H, s), 2.85 (3H, s), 3.28 (3H, s), 3.35 (3H, s), 3.64 (2H, m), 4.39 (2H, m), 7.53 (1H, dd, J=2, 8.8 Hz), 7.68 (1H, d, J=8.8 Hz), 8.33 (1H, d, J=2 Hz), 8.44 (2H, s), 9.97 (1H, s), 12.21 (1H, s), 15.11 (1H, brs) |
| 8 | $OHCNH(CH_2)_2CO$— | Yield: 54% (based on 9-hydroxyellipticine)<br>Yellow Powder<br>FAB-MS (m/z): 362 (MH⁺)<br>NMR (DMSO-$d_6$) δ: 2.39 (3H, s), 2.78 (3H, s), 2.86 (2H, m), 3.20 (3H, s), 3.55 (2H, m), 7.41 (1H, dd, J=2.2, 9 Hz), 7.61 (1H, d, J=9 Hz), 8.13 (1H, brs), 8.16 (1H, d, J=2.2 Hz), 8.32 (1H, brs), 8.36 (1H, d, J=6.9 Hz), 8.41 (1H, d, J=6.9 Hz), 9.89 (1H, s), 12.1 (1H, s) |

EXAMPLE 9

(1) To dimethylformamide (140 ml) are added glutaric acid monobenzyl ester (2.14 g), 1-hydroxybenzotriazole (1.30 g) and dicyclohexylcarbodiimide (2.38 g), and the mixture is stirred at room temperature for 4 hours. To the mixture is added 9-hydroxyellipticine (2.10 g), and the mixture is stirred at room temperature overnight. Thereafter, the same procedures as Example 2-(1) is repeated to give 9-[4-(benzyloxycarbonyl)butyryloxy]ellipticine (2.25 g) as yellow powder.
Yield: 60.3%
FAB-MS (m/z): 467 (MH⁺)
NMR (DMSO-$d_6$) δ: 1.99 (2H, m), 2.56 (2H, t, J=7 Hz), 2.72 (2H, t, J=7 Hz), 2.79 (3H, s), 3.21 (3H, s), 5.14 (2H, s), 7.29 (1H, dd, J=2.1, 8.6 Hz), 7.39 (5H, m), 7.56 (1H, d, J=8.6 Hz), 7.93 (1H, d, J=6.0 Hz), 8.11 (1H, d, J=2.1 Hz), 8.44 (1H, d, J=6.0 Hz), 9.7 (1H, s)

(2) The above product (1.18 g) and methanesulfonic acid (243 mg) are dissolved in 50% aqueous methanol (70 ml), and thereto is added 10% palladium-carbon (1 g). The mixture is subjected to hydrogenation at room temperature under atmospheric pressure. The reaction solution is filtered, and the filtrate is concentrated under reduced pressure, and to the residue is added ethanol-acetone (1:10). The precipitated powder is collected, and dried to give 9-(4-carboxylbutyryloxy)ellipticine methanesulfonate (592 mg) as yellow powder.
Yield: 49.5%
FAB-MS (m/z): 377 (MH⁺)
NMR (DMSO-$d_6$) δ: 1.95 (2H, m), 2.39 (3H, s), 2.43 (2H, m), 2.74 (2H, m), 2.77 (3H, s), 3.19 (3H, s), 7.38 (1H, dd, J=2.0, 8.8 Hz), 7.60 (1H, d, J=8.8 Hz), 8.11 (1H, d, J=2.0 Hz), 8.34 (1H, t, J=7 Hz), 8.40 (1H, d, J=7 Hz), 9.87 (1H, s), 12.07 (1H, s), 15.0 (2H, brs)

EXAMPLES 10–18

The corresponding starting compounds are treated in the same manner as in Example 9-(1) to give the compounds listed in Table 2, which are further treated in the same manner as in Example 9-(2) to give the compounds listed in Table 3. When 1.5–3 equivalents of conc. hydrochloric acid is used instead of methanesulfonic acid in 9-(2), there are obtained the hydrochlorides of the desired compounds.

TABLE 2

[Structure: R-C(=O)-O- attached to a carbazole/pyridocarbazole core with CH₃ groups and N, NH]

| Ex. No. | RCO— | Physical Properties |
|---|---|---|
| 10-1 | Bzl—OOC—CH₂CH₂CO— | Yield: 70%<br>Yellow Powder<br>FAB-MS (m/z): 453 (MH⁺)<br>NMR (DMSO-d₆) δ: 2.79 (3H, s), 2.83 (2H, m), 2.96 (2H, m), 3.20 (3H, s), 5.18 (2H, s), 7.23 (1H, dd, J=2.2, 8.7 Hz), 7.3–7.4 (5H, m), 7.56 (1H, d, J=8.7 Hz), 7.93 (1H, d, J=6.0 Hz), 8.07 (1H, d, J=2.2 Hz), 8.44 (1H, d, J=6.0 Hz), 9.70 (1H, s), 11.46 (1H, NH) |
| 11-1 | Bzl-OOCCH₂—OCOCH₂CH₂CO— | Yield: 70%<br>Yellow Powder<br>FAB-MS (m/z): 511 (MH⁺)<br>NMR (DMSO-d₆) δ: 2.79 (3H, s), 2.87 (2H, m), 2.95 (2H, m), 3.21 (3H, s), 4.83 (2H, s), 5.20 (2H, s), 7.28 (1H, dd, J=2.1, 8.7 Hz), 7.38 (5H, m), 7.56 (1H, d, J=8.7 Hz), 7.92 (1H, d, J=6.0 Hz), 8.10 (1H, d, J=2.1 Hz), 8.44 (1H, d, J=6.0 Hz), 9.69 (1H, s), 11.45 (1H, NH) |
| 12-1 | Z—NH<br>\|<br>C₂H₅CHCHCO—<br>\|<br>CH₃<br>(N—Z—L—Ile—) | Yield: 56%<br>Yellow Powder<br>FAB-MS (m/z): 510 (MH⁺)<br>NMR (DMSO-d₆) δ: 0.96 (3H, m), 1.07 (3H, d, J=6.8 Hz), 1.4 (1H, m), 1.6 (1H, m), 2.05 (1H, m), 2.79 (3H, s), 3.19 (3H, s), 4.32 (1H, m), 5.20 (2H, s), 7.24 (1H, m), 7.4 (5H, m), 7.59 (1H, d, J=8.8 Hz), 7.95 (3H, m), 8.45 (1H, d, J=6 Hz), 9.70 (1H, s), 11.48 (1H, s) |
| 13-1 | Bzl—OCH₂CO— | Yield: 53%<br>Yellow Powder<br>FAB-MS (m/z): 411 (MH⁺)<br>NMR (DMSO-d₆) δ: 2.79 (3H, s), 3.23 (3H, s), 4.55 (2H, s), 4.71 (2H, s), 7.3–7.5 (6H, m), 7.58 (1H, d, J=8.6 Hz), 7.92 (1H, d, J=6.0 Hz), 8.17 (1H, d, J=2.2 Hz), 8.44 (1H, d, J=6.0 Hz), 9.70 (1H, s), 11.47 (1H, s) |
| 14-1 | Bzl—OOC—(CH₂)₅CO— | Yield: 64%<br>Yellow Powder<br>FAB-MS (m/z): 495 (MH⁺)<br>NMR (DMSO-d₆) δ: 1.43 (2H, m), 1.67 (4H, m), 2.42 (2H, t, J=7 Hz), 2.64 (2H, t, J=7 Hz), 2.79 (3H, s), 3.21 (3H, s), 5.11 (2H, s), 7.28 (1H, dd, J=2, 9 Hz), 7.37 (5H, m), 7.56 (1H, d, J=9 Hz), 7.93 (1H, d, J=6 Hz), 8.08 (1H, d, J=2 Hz), 8.44 (1H, d, J=6 Hz), 9.70 (1H, s), 11.47 (1H, s) |
| 15-1 | CH₃<br>\|<br>Bzl—OOCCH₂CCH₂CO—<br>\|<br>CH₃ | Yield: 55%<br>Brown Powder<br>EI-MS (m/z): 494 (M⁺)<br>NMR (DMSO-d₆) δ: 1.21 (6H, s), 2.58 (2H, s), 2.73 (2H, s), 2.79 (3H, s), 3.19 (3H, s), 5.14 (2H, s), 7.24 (1H, dd, J=2.2, 8.7 Hz), 7.3–7.4 (5H, m), 7.55 (1H, d, J=8.7 Hz), 7.92 (1H, d, J=5.9 Hz), 8.04 (1H, d, J=2.2 Hz), 8.44 (1H, d, J=5.9 Hz), 9.69 (1H, s), 11.45 (1H, s) |
| 16-1 | CH₃<br>\|<br>Bzl—OOCCH₂CH₂CCO—<br>\|<br>CH₃ | Yield: 54%<br>Yellow Powder<br>FAB-MS (m/z): 495 (MH⁺)<br>NMR (DMSO-d₆) δ: 1.36 (6H, s), 2.04 (2H, brt, J=8.1 Hz), 2.54 (2H, brt, J=7.8 Hz), 2.79 (3H, s), 3.20 (3H, s), 5.13 (2H, s), 7.25 (1H, dd, J=2.3, 8.6 Hz), 7.32–7.41 (5H, m), 7.56 (1H, d, J=8.6 Hz), 7.93 (1H, d, J=6.2 Hz), 8.04 (1H, d, J=2.2 Hz), 8.44 (1H, d, J=5.9 Hz), 9.69 (1H, s), 11.47 (1H, s) |

TABLE 2-continued

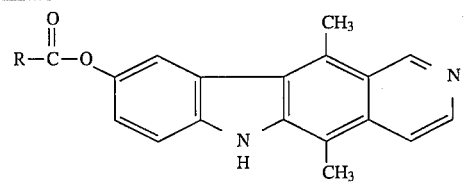

| Ex. No. | RCO— | Physical Properties |
|---|---|---|
| 17-1 | Bzl—OOC—CH$_2$OCH$_2$CO— | Yield: 37%<br>Yellow Powder<br>FAB-MS (m/z): 469 (MH$^+$)<br>NMR (DMSO-d$_6$) δ: 2.80 (3H, s), 3.23 (3H, s),<br>4.45 (2H, s), 4.61 (2H, s), 5.21 (2H, s), 7.3–7.45<br>(6H, m), 7.57 (1H, d, J=9 Hz), 7.93 (1H, d, J=6<br>Hz), 8.18 (1H, d, J=2 Hz), 8.44 (1H, d, J=6 Hz),<br>9.70 (1H, s), 11.47 (1H, s) |

Bzl: Benzyl group
Z: Benzyloxycarbonyl group

TABLE 3

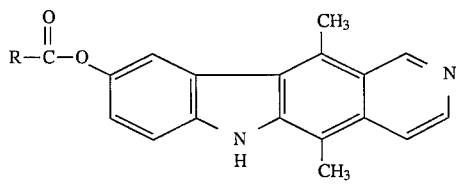

| Ex. No. | RCO— | Physical Properties |
|---|---|---|
| 10-2 | HOOCCH$_2$CH$_2$CO— | Form: Methanesulfonate<br>Yield: 77%, Yellow Powder<br>FAB-MS (m/z): 363 (MH$^+$)<br>NMR (DMSO-d$_6$) δ: 2.39 (3H, s), 2.69 (2H, m),<br>2.78 (3H, s), 2.91 (2H, m), 3.19 (3H, s), 7.36<br>(1H, dd, J=2.4, 8.8 Hz), 7.62 (1H, d, J=8.3 Hz),<br>8.09 (1H, d, J=2.4 Hz), 8.37 (2H, brm), 9.89<br>(1H, s), 12.1 (1H, s), 12.3 (1H, brs), 15.0 (1H,<br>brs) |
| 11-2 | HOOCCH$_2$OCO—CH$_2$CH$_2$CO— | Form: Methanesulfonate<br>Yield: 83%, Yellow Powder<br>FAB-MS (m/z): 421 (MH$^+$)<br>NMR (DMSO-d$_6$) δ: 2.38 (3H, s), 2.79 (3H, s),<br>2.88 (2H, m), 2.96 (2H, m), 3.21 (3H, s), 4.66<br>(2H, s), 7.38 (1H, dd, J=2.4, 8.8 Hz), 7.63<br>(1 H,d, J=8.8 Hz), 8.12 (1H, d, J=2.4 Hz), 8.37<br>(1H, d, J=7.3 Hz), 8.42 (1H, d, J=7.3 Hz), 9.90<br>(1H, s), 12.10 (1H, NH), 13.00 (1H, brs), 14.50<br>(1H, brs) |
| 12-2 | C$_2$H$_5$CHCHCO—<br>with NH$_2$ and CH$_3$ substituents<br>(L—Ile—) | Form: Dimethanesulfonate<br>Yield: 79%, Yellow Powder<br>FAB-MS (m/z): 376 (MH$^+$)<br>NMR (DMSO-d$_6$) δ: 1.04 (3H, t, J=7.3 Hz),<br>1.15 (3H, d, J=6.8 Hz), 1.5 (1H, m), 1.7 (1H, m),<br>2.14 (1H, m), 2.38 (6H, s), 2.88 (3H, s),<br>3.30 (3H, s), 4.35 (1H, m), 7.49 (1H, dd, J=2,<br>8.8 Hz), 7.76 (1H, d, J=8.8 Hz), 8.25 (1H, d,<br>J=2 Hz), 8.48 (2H, m), 8.64 (3H, brs), 10.01<br>(1H, s), 12.3 (1H, s), 15.2 (1H, brs) |
| 13-2 | HOCH$_2$CO— | Form: Hydrochloride<br>Yield: 74%, Yellow Powder<br>FAB-MS (m/z): 321 (MH$^+$)<br>NMR (DMSO-d$_6$) δ: 2.77 (3H, s), 3.17 (3H, s),<br>4.42(2H, s), 5.7 (1H, brs), 7.38 (1H, dd,<br>J=2.0, 8.6 Hz), 7.61 (1H, d, J=8.6 Hz), 8.11<br>(1H, d, J=2.0 Hz), 8.30 (1H, d, J=6.7 Hz),<br>8.38 (1H, d, J=6.7 Hz), 9.84 (1H, s), 12.3 (1H, s) |
| 14-2 | HOOC(CH$_2$)$_5$CO— | Form: Hydrochloride<br>Yield: 80%, Yellow Powder<br>FAB-MS (m/z): 405 (MH$^+$)<br>NMR (DMSO-d$_6$) δ:1.45 (2H, m), 1.61 (2H, m), |

TABLE 3-continued

[Structure: R—C(=O)—O— attached to ellipticine core with CH₃ groups, NH, and N]

| Ex. No. | RCO— | Physical Properties |
|---|---|---|
| | | 1.74 (2H, m), 2.29 (2H, t, J=7 Hz), 2.68 (2H, t, J=7 Hz), 2.77 (3H, s), 3.18 (3H, s), 7.35 (1H, dd, J=2, 9 Hz), 7.59 (1H, d, J=9 Hz), 8.07 (1H, d, J=2 Hz), 8.31 (1H, d, J=7 Hz), 8.38 (1H, d, J=7 Hz), 9.85 (1H, s), 12.1 (1H, br), 12.3 (1H, s), 15.7 (1H, brs) |
| 15-2 | HOOCCH₂—C(CH₃)(CH₃)—CH₂CO— | Form: Hydrochloride<br>Yield: 73%, Yellow Powder<br>FAB-MS (m/z): 405 (MH⁺)<br>NMR (DMSO-d₆) δ: 1.23 (6H, s), 2.44 (2H, s), 2.77 (2H, s), 2.82 (3H, s), 3.23 (3H, s), 7.37 (1H, dd, J=2.2, 8.7 Hz), 7.65 (1H, d, J=8.7 Hz), 8.10 (1H, d, J=2.2 Hz), 8.37 (1H, d, J=7 Hz), 8.41 (1H, d, J=7 Hz), 9.89 (1H, s), 12.3 (1H, s), 15.6 (1H, brs) |
| 16-2 | HOOCCH₂CH₂C(CH₃)(CH₃)CO— | Form: Hydrochloride<br>Yield: 90%, Yellow Powder<br>FAB-MS (m/z): 405 (MH⁺)<br>NMR (DMSO-d₆) δ: 1.37 (6H, s), 2.01 (2H, brt, J=8.1 Hz), 2.40 (2H, brt, J=8.1 Hz), 2.81 (3H, s), 3.23 (3H, s), 7.33 (1H, dd, J=2.2, 8.6 Hz), 7.63 (1H, d, J=8.7 Hz), 8.06 (1H, d, J=2.1 Hz), 8.35 (1H, d, J=7.0 Hz), 8.40 (1H, d, J=7.0 Hz), 9.90 (1H, s), 12.32 (1H, s) |
| 17-2 | HOOCCH₂OCH₂CO— | Form: Hydrochloride<br>Yield: 43%, Yellow Powder<br>FAB-MS (m/z): 379 (MH⁺)<br>NMR (DMSO-d₆) δ: 2.84 (3H, s), 3.26 (3H, s), 4.29 (2H, s), 4.60 (2H, s), 7.45 (1H, dd, J=2, 9 Hz), 7.67 (1H, d, J=9 Hz), 8.24 (1H, d, J=2 Hz), 8.39 (1H, d, J=7 Hz), 8.43 (1H, d, J=7 Hz), 9.93 (1H, s), 12.35 (1H, s), 12.8 (1H, brs), 15.6 (1H, brs) |
| 18-2 | HOOC(CH₂)₃CO— | Form: Hydrochloride<br>Yield: 45% (based on 9-hydroxyellipticine)<br>Yellow Powder<br>FAB-MS (m/z): 377 (MH⁺)<br>NMR (DMSO-d₆) δ: 1.96 (2H, m), 2.44 (2H, t, J=7 Hz), 2.73 (2H, t, J=7 Hz), 2.75 (3H, s), 3.16 (3H, s), 7.35 (1H, dd, J=2, 8 Hz), 7.57 (1H, d, J=8 Hz), 8.07 (1H, d, J=2 Hz), 8.30 (1H, d, J=7 Hz), 8.36 (1H, d, J=7 Hz), 9.82 (1H, s), 12.2 (1H, brs), 12.25 (1H, s), 15.6 (1H, brs) |

EXAMPLE 19

(1) N-(t-Butoxycarbonyl)sarcosine (918 mg) and 9-hydroxyellipticine (918 mg) are treated in the same manner as in Example 9-(1) to give 9-(N-t-butoxycarbonyl-N-methyl) aminoacetoxyellipticine (1.05 g) as yellow powder.
Yield: 69%
FAB-MS (m/z): 434 (MH⁺)
NMR (DMSO-d₆) δ: 1.46 (9H, s), 2.79 (3H, s), 2.98 (3H, m), 3.21 (3H, s), 4.32 (2H, m), 7.31 (1H, m), 7.60 (1H, m), 7.93 (1H, d, J=6.0 Hz), 8.09 (1H, m), 8.44 (1H, d, J=6.0 Hz), 9.7 (1H, s), 11.5 (1H, brs)

(2) The above product (1.00 g) is added to dioxane (10 ml), and thereto is added with stirring 15% hydrochloric acid-dioxane solution (5 ml) under ice-cooling. The reaction solution is stirred at room temperature for 3 hours, and thereto is added ether (100 ml). The insoluble products are collected by filtration, washed, and dried to give 9-methylaminoacetoxyellipticine dihydrochloride (851 mg) as yellow powder.
Yield: 91%
FAB-MS (m/z): 334 (MH⁺)
NMR (D₂O) δ: 1.88 (3H, s), 2.01 (3H, s), 2.99 (3H, s), 4.38 (2H, s), 6.57 (1H, d, J=8.8 Hz), 6.79 (1H, dd, J=2.0, 8.8 Hz), 7.02 (1H, d, J=2.0 Hz), 7.35 (d, J=6.8 Hz), 7.57 (1H, d, J=6.8 Hz), 8.44 (1H, s)

EXAMPLES 20–29

The corresponding starting compounds are treated in the same manner as in Example 19-(1) to give the compounds listed in Table 4, which are further treated in the same manner as in Example 19-(2) to give the compounds listed in Table 5.

TABLE 4

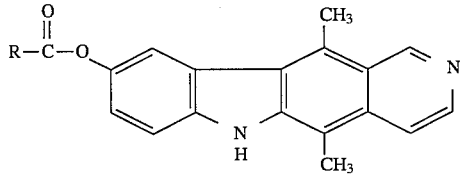

| Ex. No. | RCO— | Physical Properties |
|---|---|---|
| 20-1 | Boc—NH—C(CH₃)₂—CO— | Yield: 55%, Yellow Powder<br>FAB-MS (m/z): 448 (MH⁺)<br>NMR (DMSO-$d_6$) δ: 1.49 (9H, s), 1.53 (6H, s), 2.79 (3H, s), 3.20 (3H, s), 7.25 (1H, dd, J=2.2, 8.8 Hz), 7.58 (1H, d, J=8.8 Hz), 7.64 (1H, brs), 7.93 (1H, d, J=6 Hz), 8.01 (1H, d, J=2.2 Hz), 8.44 (1H, d, J=6 Hz), 9.70 (1H, s), 11.45 (1H, s) |
| 21-1 | Boc—NH—CH(CH₃)—CO—<br>(N—Boc—L—Ala—) | Yield: 66%, Yellow Powder<br>FAB-MS (m/z): 434 (MH⁺)<br>NMR (DMSO-$d_6$) δ: 1.46 (9H, s), 1.48 (3H, d), 2.80 (3H, s), 3.20 (3H, s), 4.32 (1H, m), 7.27 (1H, dd, J=2, 8 Hz), 7.58 (1H, d, J=8 Hz), 7.92 (1H, d, J=5.9 Hz), 8.04 (1H, d, J=2 Hz), 8.44 (1H, d, J=5.9 Hz), 9.70 (1H, s), 11.47 (1H, s) |
| 22-1 | Boc—NH—CH(CH(CH₃)₂)—CO—<br>(N—Boc—D—Val—) | Yield: 73%, Yellow Powder<br>FAB-MS (m/z): 462 (MH⁺)<br>NMR (DMSO-$d_6$) δ: 1.07 (6H, d, J=6.8 Hz), 1.47 (9H, s), 2.26 (1H, m), 2.79 (3H, s), 3.19 (3H, s), 4.13 (1H, m), 6.64 (1H, brd), 7.26 (1H, dd, J=2.0, 8.8 Hz), 7.59 (1H, d, J=8.8 Hz), 7.92 (1H, brd), 7.99 (1H, d, J=2.0 Hz), 8.42 (1H, m), 9.69 (1H, s), 11.48 (1H, s) |
| 23-1 | 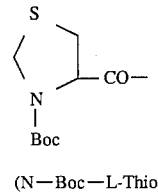<br>(N—Boc—L-Thiopro-) | Yield: 77%, Yellow Powder<br>FAB-MS (m/z): 478 (MH⁺)<br>NMR (DMSO-$d_6$) δ: 1.49 (9H, s), 2.79 (3H, s), 3.21 (3H, s), 3.60 (2H, m), 4.52 (1H, d, J=9.0 Hz), 4.63 (1H, d, J=9.0 Hz), 4.99 (1H, m), 7.30 (1H, dd, J=2,9 Hz), 7.61 (1H, d, J=9 Hz), 7.93 (1H, d, J=6 Hz), 8.08 (1H, brs), 8.44 (1H, d, J=6 Hz), 9.70 (1H, s), 11.5 (1H, s) |
| 24-1 | t-Bu—OOC—CH(Boc—NH)—CH₂CH₂CO—<br>(O¹-t-Bu—N—Boc-δ-L—Glu—) | Yield: 59%, Yellow Powder<br>FAB-MS (m/z): 548 (MH⁺)<br>NMR (DMSO-$d_6$) δ: 1.42 (9H, s), 1.44 (9H, s), 1.95 (1H, m), 2.11 (1H, m), 2.7–2.8 (2H, m), 2.79 (3H, s), 3.22 (3H, s), 4.00 (1H, m), 7.29 (1H, dd, J=2.0, 8.8 Hz), 7.57 (1H, d, J=8.8 Hz), 7.93 (1H, d, J=6.4 Hz), 8.12 (1H, d, J=2.0 Hz), 8.44 (1H, d, J=6.4 Hz), 9.70 (1H, s), 11.46 (1H, s) |
| 25-1 | C₂H₅OOC—CH(Boc—NH)—CH₂CO—<br>(L-isomer) | Yield: 72%, Yellow Powder<br>FAB-MS (m/z): 506 (MH⁺)<br>NMR (DMSO-$d_6$) δ: 1.24 (3H, t, J=7.1 Hz), 1.43 (9H, s), 2.79 (3H, s), 2.99 (1H, dd, J=8.0, 16.2 Hz), 3.15 (1H, dd, J=6.1, 16.2 Hz), 3.22 (3H, s), 4.17 (2H, q, J=7.1 Hz), 4.55 (1H, m), 7.30 (1H, dd, J=2.2, 8.6 Hz), 7.53 (1H, brs), 7.58 (1H, d, J=8.6 Hz), 7.94 (1H, d, J=6.0 Hz), 8.11 (1H, d, J=2.2 Hz), 8.44 (1H, d, J=6.0 Hz), 9.7 (1H, s), 11.5 (1H, NH) |
| 26-1 | CH₃O(CH₂)₂OCO—CH(Boc—NH)—CH₂CO—<br>(L-isomer) | Yield: 70%, Yellow Powder<br>FAB-MS (m/z): 536 (MH⁺)<br>NMR (DMSO-$d_6$) δ: 1.43 (9H, s), 2.80 (3H, s), 3.00 (1H, dd, J=8.2,16.3 Hz), 3.16 (1H, dd, J=6.0, 16.3 Hz), 3.23 (3H, s), 3.28 (3H, s), 3.57 (2H, m), 4.25 (2H, m), 4.58 (1H, m), 7.30 (1H, dd, J=2.2, 8.6 Hz), 7.56 (1H, brs), 7.57 (1H, d, J=8.6 Hz) 7.93 (1H, d, J=6.0 Hz), 8.12 (1H, d, J=2.2 Hz), 8.44 (1H, d, J=6.0 Hz), 9.70 (1H, s), 11.47 (1H, NH) |

TABLE 4-continued

[Structure: R-C(=O)-O- attached to a carbazole-isoquinoline fused ring system with two CH₃ groups and NH]

| Ex. No. | RCO— | Physical Properties |
|---|---|---|
| 27-1 | Boc—NH—C(CH₃)(CH₃)—CONHCH₂CO— | Yield: 18%, Yellow Powder<br>FAB-MS (m/z): 505 (MH⁺)<br>NMR (DMSO-d₆) δ: 1.37, 1.38 (15 H, each s), 2.80 (3H, s), 3.22 (3H, s), 4.15 (2H, d, J=5.8 Hz), 6.93 (1H, brs), 7.29 (1H, dd, J=2.2, 8.6 Hz), 7.58 (1H, d, J=8.6 Hz), 7.94 (1H, d, J=6.0 Hz), 8.09 (1H, d, J=2.2 Hz), 8.13 (1H, t, J=5.8 Hz), 8.44 (1H, d, J=6.0 Hz), 9.71 (1H, s), 11.46 (1H, NH) |
| 28-1 | Boc—NHCH₂CH₂—CONHCHCO—<br>                                     CH₃—CH—CH₃<br>(L-isomer) | Yield: 67%, Yellow Powder<br>FAB-MS (m/z): 533 (MH⁺)<br>NMR (DMSO-d₆) δ: 1.07 (3H, d, J=6.8 Hz), 1.08 (3H, d, J=6.8 Hz), 1.37 (9H, s), 2.31 (1H, m), 2.43 (2H, m), 2.79 (3H, s), 3.19 (2H, m), 3.22 (3H, s), 4.47 (1H, m), 6.76 (1H, m), 7.27 (1H, dd, J=2.2, 8.7 Hz), 7.58 (1H, d, J=8.7 Hz), 7.93 (1H, d, J=6.0 Hz), 8.02 (1H, d), J=2.2 Hz), 8.42 (2H, m), 9.70 (1H, s), 11.5 (1H, NH) |
| 29-1 | t-Bu-OOC(CH₂)₄CO— | Yield: 62%<br>Yellow Powder<br>FAB-MS (m/z): 447 (MH⁺)<br>NMR (DMSO-d₆) δ: 1.43 (9H, s), 1.68 (4H, m), 2.29 (2H, t, J=7 Hz), 2.67 (2H, t, J=7 Hz), 2.79 (3H, s), 3.22 (3H, s), 7.28 (1H, dd, J=2, 9 Hz), 7.56 (1H, d, J=9 Hz), 7.93 (1H, d, J=6 Hz), 8.09 (1H, d, J=2 Hz), 8.44 (1H, d, J=6 Hz), 9.70 (1H, s), 11.43 (1H, s) |

Boc: t-Butoxycarbonyl group
t-Bu: t-Butyl group

TABLE 5

[Structure: R-C(=O)-O- attached to a carbazole-isoquinoline fused ring system with two CH₃ groups and NH]

| Ex. No. | RCO— | Physical Properties |
|---|---|---|
| 20-2 | NH₂—C(CH₃)(CH₃)—CO— | Form: Dihydrochloride<br>Yield: 98%, Yellow Powder<br>FAB-MS (m/z): 349 (MH⁺)<br>NMR (D₂O) δ: 1.89 (6H, s), 1.96 (3H, s), 2.07 (3H, s), 6.63 (1H, d, J=8.8 Hz), 6.80 (1H, dd, J=2.0, 8.8 Hz), 6.98 (1H, d, J=2.0 Hz), 7.43 (1H, d, J=6.8 Hz), 7.65 (1H, d, J=6.8 Hz), 8.54 (1H, s) |
| 21-2 | NH₂—CH(CH₃)—CO—<br>(L—Ala—) | Form: Dihydrochloride<br>Yield: 53%, Yellow Powder<br>FAB-MS (m/z): 334 (MH⁺)<br>NMR (DMSO-d₆) δ: 1.69 (3H, d, J=6.8 Hz), 2.86 (3H, s), 3.28 (3H, s), 4.44 (1H, m), 7.47 (1H, brd), 7.72 (1H, brd), 8.30 (1H, brs), 8.45 (2H, m), 8.86 (3H, brs), 9.94 (1H, s), 12.41 (1H, s) |

TABLE 5-continued

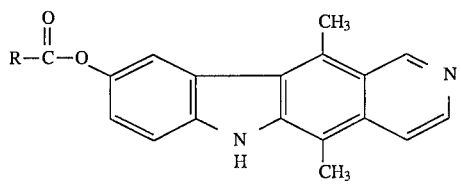

| Ex. No. | RCO— | Physical Properties |
|---|---|---|
| 22-2 | CH$_3$—CH—CH$_3$<br>　　　　｜<br>NH$_2$—CH—CO—<br><br>(D—Val—) | Form: Dihydrochloride<br>Yield: 43%, Yellow Powder<br>FAB-MS (m/z): 362 (MH$^+$)<br>NMR (DMSO-d$_6$) δ: 1.19 (3H, d, J=7 Hz), 1.21 (3H, d, J=7 Hz), 2.44 (1H, m), 2.82 (3H, s), 3.22 (3H, s), 4.18 (1H, d, J=5.4 Hz), 7.44 (1H, dd, J=2.0, 8.8 Hz), 7.67 (1H, d, J=8.8 Hz), 8.24 (1H, d, J=2.0 Hz), 8.34 (1H, d, J=6.8 Hz), 8.42 (1H, d, J=6.8 Hz), 9.04 (3H, brs), 9.90 (1H, s), 12.43 (1H, s), 15.5 (1H, brs) |
| 23-2 | (L-Thiopro-) thiazolidine-COO— structure | Form: Dihydrochloride<br>Yield: 87%, Yellow Powder<br>FAB-MS (m/z): 378 (MH$^+$)<br>NMR (D$_2$O) δ: 1.82 (3H, s), 1.90 (3H, s), 3.68 (2H, m), 4.57 (1H, d, J=10.3 Hz), 4.64 (1H, d, J=10.3 Hz), 5.15 (1H, t, J=6.4 Hz), 6.50 (1H, d, J=8.8 Hz), 6.72 (1H, brd, J=8.8 Hz), 6.85 (1H, brs), 7.29 (1H, d, J=6.8 Hz), 7.54 (1H, d, J=6.8 Hz), 8.38 (1H, s) |
| 24-2 | HOOC—CH—CH$_2$CH$_2$CO—<br>　　　　｜<br>　　　NH$_2$<br><br>(δ-L—Glu—) | Form: Dihydrochloride<br>Yield: 69%, Yellow Powder<br>FAB-MS (m/z): 392 (MH$^+$)<br>NMR (DMSO-d$_6$) δ: 2.28 (2H, m), 2.81 (3H, s), 2.95 (2H, m), 3.21 (3H, s), 4.18 (1H, m), 7.40 (1H, dd, J=2, 8.7 Hz), 7.63 (1H, d, J=8.7 Hz), 8.16 (1H, d, J=2 Hz), 8.34 (1H, d, J=6.9 Hz), 8.40 (1H, d, J=6.9 Hz), 8.7 (3H, brs), 9.9 (1H, s), 12.4 (1H, s) |
| 25-2 | C$_2$H$_5$OOC—CH—CH$_2$CO—<br>　　　　｜<br>　　　NH$_2$<br><br>(L-isomer) | Form: Dihydrochloride<br>Yield: 93%, Yellow Powder<br>FAB-MS (m/z): 406 (MH$^+$)<br>NMR (D$_2$O) δ: 1.40 (3H, t, J=7 Hz), 1.94 (3H, s), 2.05 (3H, s), 3.51 (2H, m), 4.46 (2H, q, J=7 Hz), 4.72 (1H, t, J=5.4 Hz), 6.68 (1H, d, J=8.8 Hz), 6.83 (1H, dd, J=2.0, 8.8 Hz), 6.96 (1H, brs), 7.43 (1H, d, J=6.8 Hz), 7.64 (1H, d, J=6.8 Hz), 8.54 (1H, s) |
| 26-2 | CH$_3$O(CH$_2$)$_2$OCO—CH—CH$_2$CO—<br>　　　　　　　｜<br>　　　　　　NH$_2$<br><br>(L-isomer) | Form: Dihydrochloride<br>Yield: 88%, Yellow Powder<br>FAB-MS (m/z): 436 (MH$^+$)<br>NMR (D$_2$O) δ: 1.96 (3H, s), 2.12 (3H, s), 3.47 (3H, s), 3.54 (2H, m), 3.85 (2H, m), 4.57 (2H, m), 4.77 (1H, m), 6.71 (1H, d, J=8.7 Hz), 6.84 (1H, dd, J=2.1, 8.7 Hz), 7.06 (1H, brs), 7.44 (1H, d, J=6.9 Hz), 7.65 (1H, d, J=6.9 Hz), 8.58 (1H, s) |
| 27-2 | 　　　CH$_3$<br>　　　｜<br>NH$_2$—C—CONHCH$_2$CO—<br>　　　｜<br>　　　CH$_3$ | Form: Dihydrochloride<br>Yield: 93%, Yellow Powder<br>FAB-MS (m/z): 405 (MH$^+$)<br>NMR (D$_2$O) δ: 1.77 (6H, s), 1.95 (3H, s), 2.08 (3H, s), 4.40 (2H, s), 6.64 (1H, d, J=8 Hz), 6.82 (1H, dd, J=2, 8 Hz), 7.06 (1H, d, J=2 Hz), 7.43 (1H, d, J=6.8 Hz), 7.63 (1H, d, J=6.8 Hz), 8.52 (1H, s) |

TABLE 5-continued

| Ex. No. | RCO— | Physical Properties |
|---|---|---|
| 28-2 | NH$_2$CH$_2$CH$_2$CONH—CH—CO—<br>　　　　　　　　　　｜<br>　　　　　　　CH$_3$—CH—CH$_3$<br><br>(L-isomer) | Form: Dihydrochloride<br>Yield: 93%, Yellow Powder<br>FAB-MS (m/z): 433 (MH$^+$)<br>NMR (D$_2$O) δ: 1.17 (6H, d, J=6.8 Hz),<br>1.94 (3H, s), 1.99 (3H, s), 2.43 (1H, m),<br>2.94 (2H, m), 3.41 (2H, m), 4.56 (1H, d,<br>J=5.9 Hz), 6.61 (1H, d, J=8 Hz), 6.70 (1H,<br>d, J=8 Hz), 6.74 (1H, s), 7.43 (1H, d, J=6.8<br>Hz), 7.65 (1H, d, J=6.8 Hz), 8.54 (1H, s) |
| 29-2 | HOOC(CH$_2$)$_4$CO— | Form: Hydrochloride<br>Yield: 84%, Yellow Powder<br>FAB-MS (m/z): 391 (MH$^+$)<br>NMR (DMSO-d$_6$) δ: 1.71 (4H, m), 2.34<br>(2H, t, J=7 Hz), 2.70 (1H, t, J=7 Hz), 2.79<br>(3H, s), 3.20 (3H, s), 7.36 (1H, dd, J=2, 9<br>Hz), 7.61 (1H, d, J=9 Hz), 8.10 (1H, d, J=2<br>Hz), 8.33 (1H, d, J=7 Hz), 8.39 (1H, d, J=7<br>Hz), 9.87 (1H, s), 12.0 (1H, br), 12.29 (1H, s)<br>15.6 (1H, brs) |

EXAMPLE 30

(1) N-Benzyloxycarbonyl-L-aspartic acid α-benzyl ester (1.72 g) and 9-hydroxyellipticine hydrochloride (1.20 g) are treated in the same manner as in Example 19-(1) to give 9-(O$^1$-benzyl-N-benzyloxycarbonyl-β-L-aspartyloxy)-ellipticine (1.40 g) as yellow powder.
Yield: 58%
FAB-MS (m/z): 602 (MH$^+$)
NMR (DMSO-d$_6$) δ: 2.79 (3H, s), 3.19 (5H, s+m), 4.73 (1H, m), 5.10 (2H, s), 5.22 (2H, s), 7.21 (1H, dd, J=2, 8.8 Hz), 7.4 (10H, m), 7.55 (1H, d, J=8.8 Hz), 7.93 (1H, d, J=6.4 Hz), 8.09 (1H, d, J=2 Hz), 8.1 (1H, brd), 8.44 (1H, d, J=6.4 Hz), 9.69 (1H, s), 11.47 (1H, s)

(2) The above product (1.19 g) is added to a mixture of 50% aqueous methanol (40 ml) and conc. hydrochloric acid (0.4 ml), and the mixture is subjected to catalytic hydrogenation using 10% palladium-carbon (0.6 g) under atmospheric pressure. The catalyst is removed by filtration, and the filtrate is concentrated under reduced pressure. To the residue is added a mixture of acetone-ethanol (10:1), and the mixture is stirred. The precipitated powder is collected by filtration, and dried to give 9-(β-L-aspartyloxy)ellipticine dihydrochloride (0.83 g) as yellow powder.
Yield: 92%
FAB-MS (m/z): 378 (MH$^+$)
NMR (D$_2$O) δ: 1.58 (6H, brs), 3.19 (1H, dd, J=5.9, 18.1 Hz), 3.31 (1H, dd, J=5.9, 18.1 Hz), 4.36 (1H, t-like, J=5.9 Hz), 6.22 (1H, m), 6.48 (1H, m), 6.54 (1H, s), 7.03 (1H, d, J=7 Hz), 7.31 (1H, brm), 8.08 (1H, s)

EXAMPLES 31–33

The corresponding starting compounds are treated in the same manner as in Example 30-(1) to give the compounds listed in Table 6, which are further treated in the same manner as in Example 30-(2) to give the compounds listed in Table 7.

TABLE 6

Structure: R—C(=O)—O— attached to a carbazole-fused isoquinoline system with two CH₃ groups and NH.

| Ex. No. | RCO— | Physical Properties |
|---|---|---|
| 31-1 | Bzl—OOCCH₂CH₂CHCO—<br>                    \|<br>                   Z—NH<br>(L-isomer) | Yield: 51%, Yellow Powder<br>FAB-MS (m/z): 616 (MH⁺)<br>NMR (DMSO-$d_6$) δ: 2.0–2.2 (1H, m), 2.2–2.4 (1H, m), 2.64 (2H, t, J=7 Hz), 2.80 (3H, s), 3.21 (3H, s), 4.4–4.5 (1H, m), 5.13, 5.14 (4H, each s), 7.2–7.4 (11H, m), 7.58 (1H, d, J=8.6 Hz), 7.94 (1H, d, J=6.3 Hz), 8.0–8.1 (2H, m), 8.44 ) |
| 32-1 | NH₂COCH₂CH₂—CH—CO—<br>                        \|<br>                      Z—NH<br>(L-isomer) | Yield: 37%, Yellow Powder<br>FAB-MS (m/z): 525 (MH⁺)<br>NMR (DMSO-$d_6$) δ: 2.0–2.4 (4H, m), 2.84 (3H, s), 3.25 (3H, s), 3.30 (2H, br), 4.40 (1H, m), 5.13 (2H, s), 7.3–7.4 (6H, m), 7.66 (1H, d, J=8.8 Hz), 8.04 (1H, d, J=7.3 Hz), 8.11 (1H, d, J=2.2 Hz), 8.24 (1H, d, J=6.6 Hz), 8.44 (1H, d, J=6.6 Hz), 9.86 (1H, s), 12.09 (1H, s) |
| 33-1 | Bzl—OOCCHCH₂CO—<br>             \|<br>          Z—N—CH₃<br>(L-isomer) | Yield: 46%<br>Yellow Powder<br>FAB-MS (m/z): 616 (MH⁺)<br>NMR (DMSO-$d_6$) δ: 2.80 (3H, s), 3.00 (3H, s), 3.19 (3H, s), 3.25 (1H, m), 3.37 (1H, m), 5.11 (1H, m), 5.16 (2H, s), 5.22 (2H, s), 7.19 (1H, dd, J=2.0, 8.5 Hz), 7.23–7.42 (10H, m), 7.54 (1H, d, J=8.5 Hz), 7.93 (1H, d, J=6 Hz), 8.07 (1H, d, J=2 Hz), 8.44 (1H, d, J=6 Hz), 9.69 (1H, s), 11.47 (1H, s) |

Bzl: Benzyl group
Z: Benzyloxycarbonyl group

TABLE 7

Structure: R—C(=O)—O— attached to the carbazole-fused isoquinoline system · dihydrochloride.

| Ex. No. | RCO— | Physical Properties |
|---|---|---|
| 31-2 | HOOCCH₂CH₂CHCO—<br>                 \|<br>               NH₂<br>(δ-L—Gln—) | Yield: 80%, Yellow Powder<br>FAB-MS (m/z): 392 (MH⁺)<br>NMR (D₂O) δ: 1.81 (3H, s), 1.86 (3H, s), 2.45 (2H, m), 2.78 (2H, t-like), 4.51 (1H, t, J=6.8 Hz), 6.47 (1H, d, J=8.8 Hz), 6.69 (1H, d-like, J=8.8 Hz), 6.77 (1H, s-like), 7.26 (1H, d, J=6.8 Hz), 7.53 (1H, d, J=6.8 Hz), 8.37 (1H, s) |
| 32-2 | NH₂COCH₂CH₂CHCO—<br>                    \|<br>                  NH₂<br>(L—Gln—) | Yield: 49%, Yellow Powder<br>FAB-MS (m/z): 391 (MH⁺)<br>NMR (D₂O) δ: 1.95 (3H, s), 2.06 (3H, s), 2.4–2.8 (4H, m), 4.56 (1H, t-like), 6.63 (1H, d, J=8.8 Hz), 6.81 (1H, dd, J=2, 8.8 Hz), 6.99 (1H, s-like), 7.42 (1H, d, J=7 Hz), 7.64 (1H, d, J=7 Hz), 8.53 (1H, s) |

TABLE 7-continued

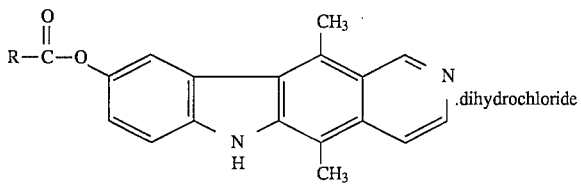

| Ex. No. | RCO— | Physical Properties |
|---|---|---|
| 33-2 | HOOCCHCH$_2$CO—<br>      |<br>    NH—CH$_3$<br><br>(L-isomer) | Yield: 62%, Orange Powder<br>FAB-MS (m/z): 392 (MH$^+$)<br>NMR (D$_2$O) δ: 2.33 (3H, s), 2.87 (3H, s), 3.25<br>1H, d, J=5.4 Hz), 3.28 (1H, d, J=5.4 Hz), 3.36<br>(3H, s), 4.1 0 (1H, t, J=5.4 Hz), 6.26 (1H, d,<br>J=7.5 Hz), 6.51 (1H, d, J=7.5 Hz), 6.61 (1H, s),<br>7.07 (1H, d, J=6.1 Hz), 7.35 (1H, d, J=6.1 Hz),<br>8.12 (1H, s) |

EXAMPLE 34

(1) To dimethylformamide (60 ml) are added 9-hydroxyellipticine hydrochloride (1.49 g), triethylamine (510 mg), N-benzyloxycarbonyl-L-aspartic acid β-benzyl ester (2.14 g), 1-hydroxybenzotriazole (338 mg) and 1-ethyl-3-(3-dimethylaminopropyl) -carbodiimide hydrochloride (1.92 g). The mixture is stirred at room temperature overnight, and concentrated under reduced pressure. To the residue is added 0.1% aqueous hydrochloric acid solution, and the mixture is stirred. The precipitated powder is collected by filtration, washed with water, and dried. The dried powder is dissolved in a mixture of chloroform-methanol (1:1), and thereto is added active carbon, and filtered. The filtrate is concentrated under reduced pressure, and to the residue is added isopropyl ether. The precipitated powder is collected by filtration, and dried to give 9-(O$^4$-benzyl-N-benzyloxycarbonyl-α-L-aspartyloxy)ellipticine hydrochloride (1.90 g) as yellow powder.

Yield: 60%

FAB-MS (m/z): 602 (MH$^+$)

NMR (DMSO-d$_6$) δ: 2.84 (3H, s), 3.04 (1H, dd, J=8.0, 16.5 Hz), 3.20 (1H, dd, J=5.5, 16.5 Hz), 3.23 (3H, s), 4.87 (1H, m), 5.14 (2H, s), 5.19 (2H, s), 7.3–7.4 (11H, m), 7.66 (1H, d, J=8.5 Hz), 8.13 (1H, d, J=2 Hz), 8.20 (1H, d, J=8.0 Hz), 8.37 (1H, d, J=7 Hz), 8.43 (1H, d, J=7 Hz), 9.92 (1H, s), 12.3 (1H, s)

(2) The above product (1.50 g)is treated in the same manner as in Example 30-(2) to give 9-(α-L-aspartyloxy)ellipticine dihydrochloride (748 mg) as yellow powder.

Yield: 71%

FAB-MS (m/z): 378 (MH$^+$)

NMR (D$_2$O) δ: 1.69 (6H, brs), 3.1–3.3 (2H, m), 4.65 (1H, t, J=4.4 Hz), 6.30 (1H, d, J=8 Hz), 6.50 (1H, d, J=8 Hz), 6.53 (1H, s), 7.15 (1H, d, J=7 Hz), 7.43 (1H, d, J=7 Hz), 8.21 (1H, s)

EXAMPLES 35–37

The corresponding starting compounds are treated in the same manner as in Example 34-(1) to give the compounds listed in Table 8, which are further treated in the same manner as in Example 34-(2) to give the compounds listed in Table 9.

TABLE 8

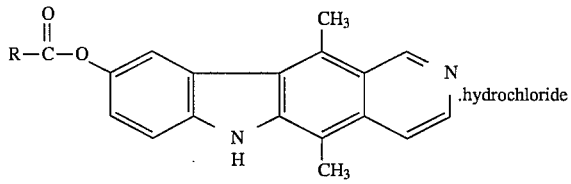

| Ex. No. | RCO— | Physical Properties |
|---|---|---|
| 35-1 | NH$_2$COCH$_2$—CH—CO—<br>            |<br>       Boc—NH<br><br>(L-isomer) | Yield: 70%, Yellow Powder<br>FAB-MS (m/z): 477 (MH$^+$)<br>NMR (DMSO-d$_6$) δ: 1.49 (9H, s), 2.82 (3H, s),<br>(2H, m), 3.23 (3H, s), 3.35 (2H, br),<br>4.73 (1H, m), 7.37 (1H, dd, J=2.0, 8.6 Hz),<br>7.68 (1H, d, J=8.6 Hz), 8.09 (1H, d, J=7.9<br>Hz), 8.12 (1H, d, J=2.0 Hz), 8.35 (1H, d,<br>J=6.9 Hz), 8.43 (1H, d, J=6.9 Hz), 9.91 (1H, s),<br>12.3 (1H, s) |

TABLE 8-continued

[Structure: R—C(=O)—O— attached to a carbazole-isoquinoline fused ring system with CH₃ groups and NH, shown as hydrochloride]

| Ex. No. | RCO— | Physical Properties |
|---|---|---|
| 36-1 | CH₃NHCO—CH—CH₂CO—<br>             \|<br>            Boc—NH<br>(L-isomer) | Yield: 38%, Yellow Powder<br>FAB-MS (m/z): 525 (MH⁺)<br>NMR (DMSO-d₆) δ: 2.66 (3H, d, J=4.4 Hz),<br>2.7–2.8 (2H, m), 2.83 (3H, s), 3.23 (3H, s),<br>4.78 (1H, m), 5.13 (2H, s), 7.36 (6H, m),<br>7.66 (1H, d, J=8.4 Hz), 7.8 (1H, brm), 7.96<br>(1H, d, J=8 Hz), 8.1 1 (1H, brs), 8.36 (1H, d,<br>J=7.0 Hz), 8.43 (1H, d, J=7.0 Hz), 9.92 (1H,s ),<br>12.3 (1H, s), 15.5 (1H, br) |
| 37-1 | Z—NH(CH₂)₄—CH—CO—<br>                 \|<br>              Z—NH<br>(L-isomer) | Yield: 65%, Yellow Powder<br>FAB-MS (m/z): 659 (MH⁺)<br>NMR (DMSO-d₆) δ: 1.51 (4H, m), 1.90 (2H, m),<br>2.86 (3H, s), 3.06 (2H, m), 3.26 (3H, s),<br>4.36 (1H, m), 5.02 (2H, s), 5.13 (2H, s), 7.3–7.4<br>(12H, m), 7.69 (1H, d, J=8.7 Hz), 8.12<br>(1H, d, J=2 Hz), 8.37 (1H, d, J=7.0 Hz), 8.44<br>(1H, d, J=7.0 Hz), 9.94 (1H, s), 12.3 (1H, s) |

Boc: t-Butoxycarbonyl group
Z: Benzyloxycarbonyl group

TABLE 9

[Structure: R—C(=O)—O— attached to carbazole-isoquinoline fused ring system with CH₃ groups and NH]

| Ex. No. | RCO— | Physical Properties |
|---|---|---|
| 35-2 | NH₂COCH₂—CH—CO—<br>            \|<br>            NH₂<br>(L—Asn—) | Form: Dihydrochloride<br>Yield: 82%, Yellow Powder<br>FAB-MS (m/z): 377 (MH⁺)<br>NMR (D₂O) δ: 1.82 (3H, s), 1.86 (3H, s),<br>3.48 (1H, dd, J=5.9, 18 Hz), 3.61 (1H, dd,<br>J=5.9,18 Hz), 4.92 (1H, t, J=5.9 Hz), 6.48<br>(1H, d, J=9 Hz), 6.74 (1H, d, J=9 Hz), 6.85<br>(1H, s), 7.28 (1H, d, J=7 Hz), 7.55 (1H, d,<br>J=7 Hz), 8.37 (1H, s) |
| 36-2 | CH₃NHCO—CH—CH₂CO—<br>             \|<br>            NH₂<br>(L-isomer) | Form: Dihydrochloride<br>Yield: 44%, Yellow Powder<br>FAB-MS (m/z): 391 (MH⁺)<br>NMR (D20) 5:1.89 (3H, s), 1.96 (3H, s),<br>2.89 (3H, s), 3.1–3.5 (2H, m), 4.74 (1H, t-like,<br>J=4 Hz), 6.56 (1H, d, J=8.3 Hz), 6.71<br>(1H, d, J=8.3 Hz), 6.82 (1H, s), 7.35 (1H, d,<br>J=6 Hz), 7.59 (1H, d, J=6 Hz), 8.44 (1H, s) |
| 37-2 | NH₂(CH₂)₄—CH—CO—<br>             \|<br>            NH₂<br>(L—Lys—) | Form: Trihydrochloride<br>Yield: 77%, Yellow Powder<br>FAB-MS (m/z): 391 (MH⁺)<br>NMR (D₂O) δ: 1.8–2.4 (6H, m), 2.07 (3H, s),<br>2.26 (3H, s), 3.26 (2H, t-like), 4.64 (1H, dd-like),<br>6.83 (1H, d, J=8.8 Hz), 7.01 (1H, dd,<br>J=2.0, 8.8 Hz), 7.28 (1H, d, J=2.0 Hz), 7.53<br>(1H, d, J=7 Hz), 7.73 (1H, d, J=7 Hz), 8.66<br>(1H, s) |

EXAMPLE 38

(1) N-(t-Butoxycarbonyl)-D-aspartic acid α-t-butyl ester (4.17 g) and 9-hydroxyellipticine hydrochloride (3.59 g) are treated in the same manner as in Example 19-(1) to give 9-(N-t-butoxycarbonyl-$O^1$-t-butyl-β-D-aspartyloxy)-ellipticine (4.28 g) as yellow powder.
Yield: 66.8%
FAB-MS (m/z): 534 (MH$^+$)
NMR (DMSO-$d_6$)δ: 1.43 (9H, s), 1.45 (9H, s), 2.80 (3H, s), 2.95 (1H, m), 3.10 (1H, m), 3.23 (3H, s), 4.42 (1H, m), 7.29 (1H, dd, J=2.2, 9 Hz), 7.43 (1H, d, J=8 Hz), 7.58 (1H, d, J=9 Hz), 7.93 (1H, d, J=6 Hz), 8.11 (1H, d, J=2.2 Hz), 8.44 (1H, d, J=6 Hz), 9.07 (1H, s), 11.47 (1H, s)

(2) The above product (1.70 g) is added to methylene chloride (20 ml), and thereto is added with stirring trifluoroacetic acid (40 ml). The mixture is stirred at room temperature for 6 hours, and concentrated. The residue is dissolved in a small amount of water, and the mixture is purified by column chromatography packed with ion-exchange resin; IRA-68 (Cl- type, Organo Corporation) (solvent; water). The desired fractions are combined, and concentrated under reduced pressure. To the residue is added acetone, and the precipitated powder is collected by filtration, washed, and dried to give 9-(β-D-aspartyloxy) ellipticine hydrochloride (995 mg) as yellow powder.
Yield: 75.6%
FAB-MS (m/z): 378 (MH$^+$)
NMR ($D_2O$) δ: 1.67 (3H, s), 1.73 (3H, s), 3.15 (1H, dd, J=5.9, 17.6 Hz), 3.29 (1H, dd, J=5.4, 17.6 Hz), 4.18 (1 H, dd, J=5.4, 5.9 Hz), 6.30 (1H, d, J=8 Hz), 6.55 (1H, d, J=8 Hz), 6.68 (1H, brs), 7.12 (1H, d, J=6.8 Hz), 7.39 (1H, d, J=6.8 Hz), 8.18 (1H, s)

What is claimed is:

1. An elliptidne compound of the formula (I):,

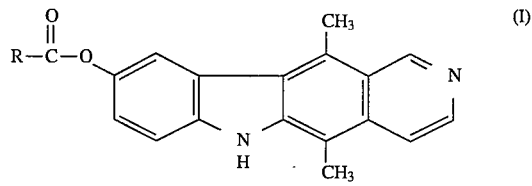

wherein R is a lower alkyl group which is substituted by a carboxyl group, a Ioweralkoxycarbonyl group, a lower alkoxy-substituted lower alkoxycarbonyl group or a carboxyl substituted lower alkoxycarbonyl group or a pharmaceutically acceptable salt thereof.

2. The compound according to claim 1, wherein R is a lower alkyl group substituted by a carboxyl group.

3. 9-(4-Carboxylbutyryloxy)ellipticine or a pharmaceutically acceptable salt thereof.

* * * * *

UNITED STATES PATENT AND TRADEMARK OFFICE
CERTIFICATE OF CORRECTION

PATENT NO. : 5,565,569
DATED : October 15, 1996
INVENTOR(S) : Kenji TSUJIHARA et al.

It is certified that error appears in the above-indentified patent and that said Letters Patent is hereby corrected as shown below:

Claim 1, column 30, line 8, "elliptidne" should read --ellipticine--.

Claim 1, column 30, line 18, "Ioweralkoxycarbonyl" should read --lower alkoxycarbonyl--.

Signed and Sealed this

Fifteenth Day of July, 1997

Attest:

BRUCE LEHMAN

*Attesting Officer*   *Commissioner of Patents and Trademarks*